US008852874B2

(12) United States Patent
Olas et al.

(10) Patent No.: US 8,852,874 B2
(45) Date of Patent: Oct. 7, 2014

(54) ANTI-AMYLOID β ACTIVITY OF INTRAVENOUS IMMUNOGLOBULIN (IVIG) IN VITRO

(75) Inventors: Katarzyna Olas, Vienna (AT); Birgit Reipert, Deutsch Wagram (AT); Hans-Peter Schwarz, Vienna (AT); Hartmut Ehrlich, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 1330 days.

(21) Appl. No.: 12/392,267

(22) Filed: Feb. 25, 2009

(65) Prior Publication Data

US 2009/0221017 A1 Sep. 3, 2009

Related U.S. Application Data

(60) Provisional application No. 61/032,874, filed on Feb. 29, 2008.

(51) Int. Cl.
  *G01N 33/68* (2006.01)
  *G01N 33/50* (2006.01)
  *C12Q 1/32* (2006.01)
  *A61K 39/395* (2006.01)

(52) U.S. Cl.
  CPC ........ *G01N 33/5014* (2013.01); *G01N 33/5058* (2013.01); *G01N 33/5008* (2013.01); *G01N 33/6896* (2013.01); *G01N 2333/4709* (2013.01); *G01N 2500/10* (2013.01)
  USPC .......................... 435/7.21; 435/26; 424/130.1

(58) Field of Classification Search
  None
  See application file for complete search history.

(56) References Cited

U.S. PATENT DOCUMENTS

| | | | |
|---|---|---|---|
| 7,138,120 B2 | 11/2006 | Laursen et al. | |
| 2002/0004194 A1 | 1/2002 | Lee et al. | |
| 2002/0098173 A1 | 7/2002 | Findeis et al. | |
| 2003/0105152 A1 | 6/2003 | Ingram et al. | |
| 2005/0129695 A1 | 6/2005 | Mercken et al. | |
| 2006/0099211 A1 * | 5/2006 | Monthe et al. | 424/145.1 |

FOREIGN PATENT DOCUMENTS

| | | | |
|---|---|---|---|
| EP | 0 613 007 A2 * | 8/1994 | |
| WO | WO 2007/094668 A1 | 8/2007 | |

OTHER PUBLICATIONS

Istrin G et al. Intravenous immunoglobulin enhances the clearance of fibrillar amyloid-beta peptide. J. Neurosci. Res. 2006; 84:434-443.*
Zhang G et al. Comparison of different brands of IVIg in an in vitro model of immune neuropathy. J Neuroimmunol. 2006; 173:200-203.*

International Search Report and Written Opinion dated Aug. 18, 2009 for corresponding International Application No. PCT/US2009/035119, filed Feb. 25, 2009.
Austen et al., "Designing peptide inhibitors for oligomerization and toxicity of Alzheimer's beta-amyloid peptide," 2008, Biochemistry, vol. 47, No. 7, 1984-1992.
Du et al., "Human anti-β-amyloid antibodies block β-amyloid fibril formation and prevent β-amyloid-induced neurotoxicity," 2003, Brain, vol. 126, No. 9, 1935-1939.
McLaurin et al., "Therapeutically effective antibodies against amyloid-beta peptide target amyloid-beta residues 4-10 and inhibit cytotoxicity and fibrillogenesis," 2002, Nature Medicine, vol. 8, No. 11, 1263-1269.
Solomon et al., "Disaggregation of Alzheimer β-amyloid by site-directed mAb," 1997, PNAS, vol. 94, 41109-4112.
Solomon, "Intravenous immunoglobulin and Alzheimer's disease immunotherapy," 2007, Current Opinion in Molecular Therapeutics, vol. 7, No. 1, 79-85.
Zameer et al., "Single chain Fv antibodies against the 25-35 Abeta fragment inhibit aggregation and toxicity of Abeta42," 2006, Biochemistry, vol. 45, No. 38, 11532-11533.
Adams, G., et al., "Highly Specific in Vivo Tumor Targeting by Monovalent and Divalent Forms of 741F8 Anti-c-*erb*B-2 Single Chain Fv[1]," *Cancer Research*, vol. 53, pp. 4026-4034 (Sep. 1, 1993).
Altschul, S., et al., "Basic Local Alignment Search Tool," *J. Mol. Biol.*, vol. 215, pp. 403-410 (1990).
Altschul, S., et al., "Gapped BLAST and PSI-BLAST: a new generation of protein database search programs," *Nucleic Acids Research*, vol. 25(17), pp. 3389-3402 (1997).
Bard, F., et al., "Peripherally administered antibodies against amyloid β-peptide enter the central nervous system and reduce pathology in a mouse model of Alzheimer disease," *Nature Medicine*, vol. 6(8), pp. 916-919 (Aug. 2000).
Bourhim, M., et al., "Linear quantitation of Aβ aggregation using Thioflavin T: Reduction in fibril formation by colostrinin," *Journal of Neuroscience Methods*, vol. 160, pp. 264-268 (2007).
DeMattos, R., et al., "Peripheral anti-Aβ antibody alters CNS and plasma Aβ clearance and decreases brain Aβ burden in a mouse model of Alzheimer's disease," *PNAS*, vol. 98(15), pp. 8850-8855 (Jul. 17, 2001).
Dodel, R., et al., "Human Antibodies against Amyloid β Peptide: A Potential Treatment for Alzheimer's Disease," *Ann. Neurol*, vol. 52, pp. 253-256 (2002).
Dodel, R., et al., "Intravenous immunoglobulins containing antibodies against β-amyloid for the treatment of Alzheimer's disease," *J. Neurol Neurosurg Psychiatry*, vol. 75, pp. 1472-1474 (2004).
Du, Y., et al., "Human anti-β-amyloid antibodies block β-amyloid fibril formation and prevent β-amyloid-induced neurotoxicity," *Brain*, vol. 126, pp. 1935-1939 (2003).
Du, Y., et al., "Reduced levels of amyloid β-peptide antibody in Alzheimer disease," *Neurology*, vol. 57, pp. 801-805 (2001).
Findeis, M., et al., "Modified-Peptide Inhibitors of Amyloid β-Peptide Polymerization," *Biochemistry*, vol. 38, pp. 6791-6800 (1999).

(Continued)

*Primary Examiner* — Kimberly A Ballard
(74) *Attorney, Agent, or Firm* — Kilpatrick Townsend & Stockton LLP

(57) ABSTRACT

The present invention relates to a cell-based in vitro screening assay for identifying and selecting therapeutic agents that inhibit amyloid β-induced cytotoxicity.

20 Claims, 5 Drawing Sheets

(56) References Cited

OTHER PUBLICATIONS

Gruber, M., et al., "Efficient Tumor Cell Lysis Mediated by a Bispecific Single Chain Antibody Expressed in *Escherichia coli*," *Journal of Immunology*, vol. 152, pp. 5368-5374 (1994).

Hansen, M., et al., "Re-examination and further development of a precise and rapid dye method for measuring cell growth/cell kill," *Journal of Immunological Methods*, vol. 119, pp. 203-210 (1989).

Hardy, J., et al., "The Amyloid Hypothesis of Alzheimer's Disease: Progress and Problems on the Road to Therapeutics," *Science*, vol. 297, pp. 353-356 (Jul. 19, 2002).

Hartmann, T., et al., "Distinct sites of intracellular production for Alzheimer's disease A β40/42 amyloid peptides," *Nature Medicine*, vol. 3(9), pp. 1016-1020 (Sep. 1997).

Henikoff, S., et al., "Amino acid substitution matrices from protein blocks," *Proc. Natl. Acad. Sci. USA*, vol. 89, pp. 10915-10919 (Nov. 1992).

Hock, C., et al., "Antibodies against β-Amyloid Slow Cognitive Decline in Alzheimer's Disease," *Neuron*, vol. 38, pp. 547-554 (May 22, 2003).

Hu, S-Z, et al., "Minibody: A Novel Engineered Anti-Carcinoembryonic Antigen Antibody Fragment (Single-Chain Fv-$C_H3$) Which Exhibits Rapid, High-Level Targeting of Xenografts," *Cancer Research*, vol. 56, pp. 3055-3061 (Jul. 1, 1996).

Klein, W., et al., "Targeting small A β oligomers: the solution to an Alzheimer's disease conundrum?" *Trends in Neurosciences*, vol. 24(4), pp. 219-224 (Apr. 2001).

Kostelny, S., et al., "Formation of a Bispecific Antibody by the Use of Leucein Zippers," *The Journal of Immunology*, vol. 148(5), pp. 1547-1553 (Mar. 1, 1992).

McCartney, J., et al., "Engineering disulfide-linked single-chain Fv dimmers [(sFv')$_2$] with improved solution and targeting properties: anti-digoxin 26-10 (sFv')$_2$ and anti-c-erbB-2 741F8 (sFv')$_2$ made by protein folding and bonded through C-terminal cysteinyl peptides," *Protein Engineering*, vol. 8(3), pp. 301-314 (1994).

Needleman, S., et al., "A General Method Applicable to the Search for Similarities in the Amino Acid Sequence of Two Proteins," *J. Mol. Biol.*, vol. 48, pp. 443-453 (1970).

Nicoll, J., et al., "A β Species Removal After A $β_{42}$ Immunization," *J. Neuropathol. Exp. Neurol.*, vol. 65(11), pp. 1040-1048 (Nov. 2006).

Pack, P., et al., "Miniantibodies: Use of Amphipathic Helices to Produce Functional, Flexibly Linked Dimeric Fv Fragments with High Avidity in *Escherichia coli*," *Biochemistry*, vol. 31(6), pp. 1579-1584 (Feb. 18, 1992).

Pearson, W., et al., "Improved tools for biological sequence comparison," *Proc. Natl. Acad. Sci. USA*, vol. 85, pp. 2444-2448 (Apr. 1988).

Schenk, D., et al., "Immunization with amyloid-β attenuates Alzheimer-disease-like pathology in the PDAPP mouse," *Nature*, vol. 400, pp. 173-177 (Jul. 8, 1999).

Shearman, M., et al., "Inhibition of PC12 cell redox activity is a specific, early indicator of the mechanism of β-amyloid-mediated cell death," *Proc. Natl. Acad. Sci. USA*, vol. 91, pp. 1470-1474 (Feb. 1994).

Smith, T., et al., "Comparison of Biosequences," *Advances in Applied Mathematics*, vol. 2, pp. 483-489 (1981).

Solomon, B, et al., "Disaggregation of Alzheimer βamyloid by site-directed mAb" *Proc. Natl. Acad. Sci. USA*, vol. 94, pp. 410-4112 (Apr. 1997).

Tanzi, R.E., et al., "Clearance of Alzheimer's A β Peptide: The Many Roads to Perdition," *Neuron*, vol. 43, pp. 605-608 (Sep. 2, 2004).

Wilcock, D., et al., "Intracranially Administered Anti-A β Antibodies Reduce β-Amyloid Deposition by Mechanisms Both Independent of and Associated with Microglial Activation," *The Journal of Neuroscience*, vol. 23(9), pp. 3745-3751 (May 1, 2003).

Yin, Y., et al., "γ-Secretase Substrate Concentration Modulates the A β42/A β40 Ratio," The Journal of Biological Chemistry, vol. 282(32), pp. 23639-23644 (Aug. 10, 2007).

Zhu, Z., et al., "Remodeling domain interfaces to enhance heterodimer formation," *Protein Science*, vol. 6, pp. 781-788 (1997).

\* cited by examiner

US 8,852,874 B2

ANTI-AMYLOID β ACTIVITY OF INTRAVENOUS IMMUNOGLOBULIN (IVIG) IN VITRO

CROSS REFERENCE TO RELATED APPLICATIONS

The present application claims the benefit of U.S. Application No. 61/032,874, filed Feb. 29, 2008, which is incorporated herein by reference.

FIELD OF THE INVENTION

The present invention relates to in vitro assays for identifying compounds that act to inhibit amyloid β (Aβ) induced cytotoxicity in vitro.

BACKGROUND OF THE INVENTION

The accumulation of cytotoxic Aβ in the brain is considered to be a key pathogenic event contributing to neurodegeneration in Alzheimer's disease (AD). See, Hardy and Selkoe, (2002), *Science* 297:353-336.

Aβ is a metabolite produced during processing of a large transmembrane glycoprotein, the Aβ precursor protein (APP). The level of Aβ in the brain is controlled by the rate of production from amyloid precursor protein (APP) and the rate of clearance. See, Tanzi et al., (2004) *Neuron* 43:605-608. Aβ is formed after sequential cleavage of APP, which is a transmembrane glycoprotein of undetermined function. APP can be processed by α-, β- and γ-secretase enzymes, and the Aβ protein is generated by successive action of the β and γ secretase on APP. The C-terminal end of the Aβ peptide is produced by the action of γ-secretase, which cleaves within the transmembrane region of APP to generate a number of isoforms of 39-43 amino acid residues in length. The most common isoforms are $A\beta_{40}$ and $A\beta_{42}$. The shorter form ($A\beta_{40}$) is typically produced by a cleavage reaction that occurs in the endoplasmic reticulum, while the longer form ($A\beta_{42}$) is typically produced by a cleavage reaction in the trans-Golgi network. See, *Nat. Med.* 3(9):1016-1020 (1997). The $A\beta_{40}$ form is the more common of the two, but the $A\beta_{42}$ is more fibrillogenic and is thus more frequently associated with disease states. Mutations in APP associated with early-onset Alzheimer's have been noted to increase the relative production of $A\beta_{42}$, and thus one suggested avenue of Alzheimer's therapy involves modulating the activity of β and γ secretases to produce mainly $A\beta_{40}$—See, Yin, Y. I., et al. (2007) *J Biol. Chem.* August 10; 282(32):23639-44.

Recently it has been shown that vaccination with $A\beta_{42}$ as well as passive immunization with anti-$A\beta_{42}$ antibodies reduced brain Aβ-load and improved behavior in animal models. See, e.g., Schenk et al. (1999) *Nature* 400:173-177; DeMattos et al., (2001) *Proc. Nat'l. Acad. Sci. USA* 98:8850-8855; Bard et al. (2000) *Nat. Med.* 6:916-919; Wilcock et al. (2003) *J. Neurosci.* 23:3745-3751. Although reduced Aβ deposition (Nicoll et al. (2006) *J. Neuropathol. Exp. Neurol.* 65:1040-1048) and slower cognitive decline (Hock et al., (2003) *Neuron* 38:547-554) have been reported in clinical immunization trials involving anti-$A\beta_{42}$ antibodies in AD patients the trials also showed adverse neuroinflammatory effects as a result of the immunization.

In humans, naturally occurring antibodies against Aβ have been detected in both the cerebrospinal fluid (CSF) and the serum of healthy subjects, while significantly lower anti-Aβ antibody titers have been detected in the in CSF of AD patients. See, Du et al. (2001) *Neurology* 57:801-805.

Naturally occurring anti-$A\beta_{42}$ antibodies are detectable in commercially available human IVIG preparations and have been found to modify total Aβ and $A\beta_{42}$ levels in the CSF. See, Dodel et al. (2002) *Ann. Neurol.* 52:253-256; and Dodel et al. (2004) *J. Neurosurg. Psychiatry* 75:1472-1474. Furthermore, it has been shown previously that naturally occurring anti-Aβ antibodies, when isolated from immunoglobulins preparations, inhibit Aβ-induced cytotoxic activity in vitro (Du et al. (2003) *Brain* 126:1935-1939).

Thus, there exists a need for a method to screen and compare various agents (e.g., different lots of immunoglobulin preparations) for their ability to inhibit Aβ-induced cytotoxicity in vitro. Such a method will allow for the identification of potential drug candidates as well as pre-selection of human plasmatic (IVIG) lots suitable for treating Alzheimer's disease patients. The present invention addresses this and other needs.

BRIEF SUMMARY OF THE INVENTION

One aspect of the invention provides for an in vitro cell-based screening assay to identify agents that inhibit Aβ-induced cytotoxicity in a susceptible cell. The method comprises contacting a test cell culture with a cytotoxic Aβ aggregate and a test agent, determining the level of cytotoxicity in the test cell culture, and comparing to the level of cytotoxicity in a control cell culture. The level of cytotoxicity in the test cell culture is normalized to the level of cytotoxicity in the control cell culture and a suitable test agent that inhibits Aβ-induced cytotoxicity can thereby be selected. In some embodiments, the control cell culture is identical to the test cell culture except for the presence of the test agent. In some embodiments the control cell culture comprises the cytotoxic Aβ aggregates. In some embodiments, the control cell culture comprises the cytotoxic Aβ aggregates and a control agent that is known to inhibit Aβ-induced cytotoxicity.

In some embodiments, the Aβ peptide is 43 amino acids in length. In some embodiments, the Aβ peptide is between 39 and 43 amino acids in length. In some embodiments, the Aβ peptide is less than 39 amino acids in length. In some embodiments, the Aβ aggregate is comprised of at least an Aβ dimer. In some embodiments, the cytotoxic Aβ aggregates are characterized using a quantitative thioflavin T—binding fluorescence assay.

In some embodiments, the Aβ aggregates are used in a concentration range from about 2.5 μM to about 25 μM. In some embodiments, the concentration range of the Aβ aggregates is from about 5 μM to about ~30 μM. In some embodiments, the concentration range for the Aβ aggregates is about 10 μM to about 15 μM.

In some embodiments of the invention, the susceptible cell is a PC-12 cell. In some embodiments, a susceptible cell is identified by demonstrating that the cell exhibits a detectable cytotoxic response in the presence of a cytotoxic Aβ aggregate solution in the range of about 2.5 μM to about 25 μM. In some embodiments, the cells are adapted to grow under serum-free conditions. In some embodiments, the cells are grown in the presence of serum or a serum supplement and then switched to serum-free conditions prior to conducting the assay.

In some embodiments, the test and/or control agent are selected from the group consisting of a protein, an antibody, a peptide, a proteinaceous complex, a lipid, a carbohydrate, an IVIG lot, and a small molecule. In some embodiments, the control agent is an antibody that binds Aβ.

In some embodiments, the test agent and/or control agent are contacted to the cell culture before the cytotoxic Aβ aggregates. In some embodiments, the cytotoxic Aβ aggregates are contacted to the test and/or control cultures before the test and/or control agents. In some embodiments, the test and/or control agent is pre-mixed with the cytotoxic Aβ aggregates before contacting to the respective cell culture.

In some embodiments, the test agent and the control agent are used in equal molar concentrations. In some embodiments, the test agent and the control agent are added in a molar concentration ratio with the cytotoxic Aβ aggregates. In some embodiments, the molar concentration ratio of the agent:Aβ aggregate is from about 1:30 to about 30:1. In some embodiments, the molar concentration ratio of agent:Aβ aggregate is from about 1:5 to about 5:1. In some embodiments, the molar concentration ratio of agent:Aβ aggregate is about 1:1.

In some embodiments the level of cytotoxicity in the culture is determined by measuring the level of lactate dehydrogenase released into the culture medium. In some embodiments the level of cytotoxicity is measured by determining the level of mitochondrial dehydrogenase activity. In some embodiments the level of cytotoxicity is determined by measuring the level of apoptosis in the culture. In some embodiments, the level of cytotoxicity is measured by determining the membrane integrity of the cultured cells.

In some embodiments, a test agent is selected if it detectably reduces Aβ-induced cytotoxicity as compared to a control cell culture. In some embodiments, a test agent is selected if it reduces Aβ-induced cytotoxicity at least 5%, 10%, 20%, 30%, 40%, 50%, 60%, 70%, 80%, 90%, or more compared to a control cell culture. In some embodiments, a test agent is selected if it reduces Aβ-induced cytotoxicity at least 5%, 10%, 20%, 30%, 40%, 50%, 60%, 70%, 80%, 90% or more compared to the level of cytotoxicity in the presence of the cytotoxic Aβ aggregates alone.

In some embodiments, a test agent selected using the assay is administered to a patient having Alzheimer's disease as part of a treatment regime.

DETAILED DESCRIPTION OF THE INVENTION

Introduction

Figure 1:
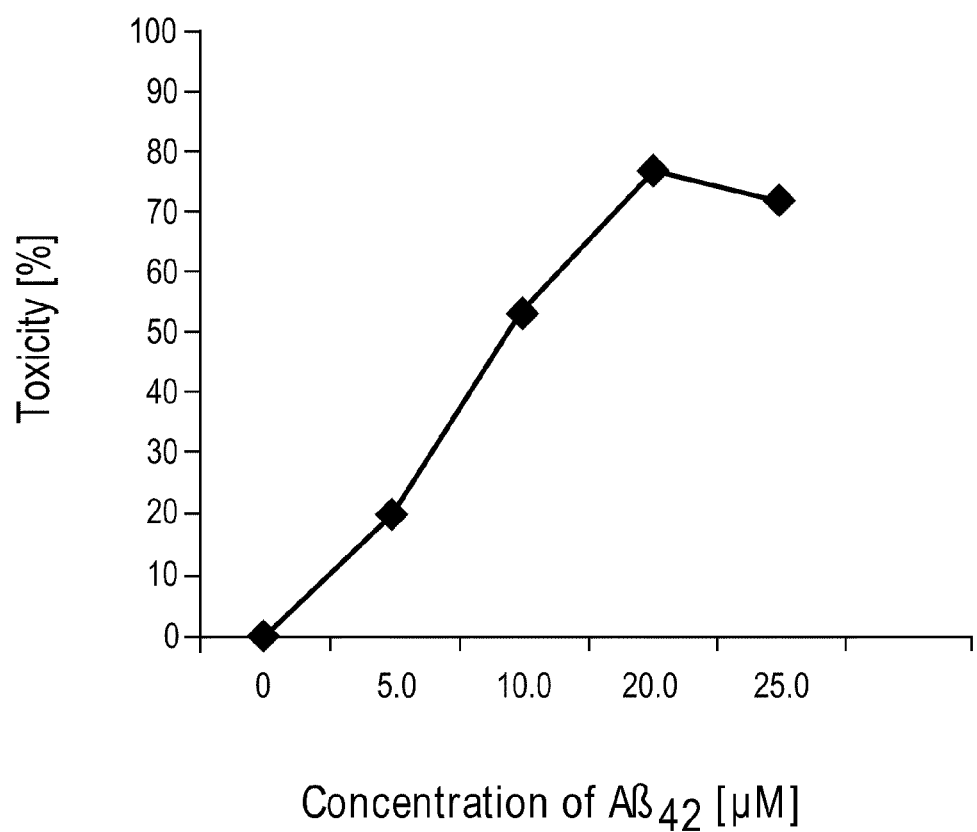
FIG. 1 shows the dose dependent $A\beta_{42}$-induced cytotoxicity in PC-12 cells in vitro. Percent toxicity was calculated according to the procedure described in Example 2.

The accumulation of cytotoxic Aβ in the brain is a key pathogenic event contributing to neurodegeneration in Alzheimer's disease (AD). Naturally occurring anti-Aβ antibodies are present in the IVIG preparations from healthy individuals, and these antibodies have been shown to modulate the total Aβ content in the CSF. However, the content of the antibodies in the IVIG preparations varies from lot to lot. Thus, there exists a need for a screening assay that allows for the comparison and pre-selection of IVIG products that are most suitable for administering to patients suffering from AD.

The present invention, as detailed herein, provides for a high-throughput cell based in vitro screening assay to identify agents that inhibit Aβ-induced cytotoxicity. The methods as disclosed herein also provide for a normalization procedure that allows for a more direct comparison of different agents and/or concentrations of the agents to inhibit Aβ-induced cytotoxicity. This normalization procedure involves an arbitrary unit assigned to a control agent, against which test agents can be directly compared. This arbitrary unit allows for the comparison of different test agents in their ability to inhibit Aβ-induced cytotoxicity in vitro, or alternatively provides a selection criteria for pre-selecting particular agents (e.g., IVIG lots) suitable for administration to a patient with AD. In addition, the methods disclosed herein provide for characterizing the Aβ aggregates used in the assays. These and other aspects of the invention are described in more detail below and in the examples.

Definitions

As used herein, the term "Amyloid-β" or "Aβ" refers to a peptide monomer that is a naturally occurring proteolytic cleavage product of the amyloid-β precursor protein (APP) or a fragment of the naturally occurring proteolytic product and is involved in formation of Aβ aggregates and β-amyloidosis. Non-limiting exemplary Aβ peptides suitable for use with the invention include natural cleavage products of APP having 39-43 amino acids (i.e. $A\beta_{1-39}$, $A\beta_{1-40}$, $A\beta_{1-41}$, $A\beta_{1-42}$, and $A\beta_{1-43}$).

As used herein, the term "aggregate" of Aβ refers to any higher order structure formed by an association of more than one Aβ monomer. A "cytotoxic aggregate" as used herein is an Aβ aggregate that induces a cytotoxic response in a susceptible cell. An aggregate can be composed of a mixture of Aβ-dimer, -trimer, -tetramer, -pentamer, all the way up to and including an Aβ-oligomerized or multimerized protein and can appear as a multimeric structure and/or assembly of molecules. Numerous assay available in the art and discussed herein can be used to detect and characterize Aβ aggregates suitable for use with the present invention. Non-limiting exemplary assays suitable for detecting and characterizing Aβ aggregates for use in the invention include fluorometric assays using the fluorescent dyes thioflavin T, or thioflavin S, optical density assays, gel electrophoresis analysis, as well as direct aggregate visualization using electron microscopy.

As used herein, the term "amyloid β-induced cytotoxicity" refers to the ability of the Aβ aggregates to induce a harmful effect that results in a detectable injury to a susceptible cell type in vitro. Non-limiting examples of detectable injuries can include loss of membrane integrity, altered ion flux, early markers of apoptosis, and cell death. Typically, the cytotoxic response is detected using a cell viability assay as described herein. For example, an increase in the level of lactate dehydrogenase detectable in the culture medium following exposure to the Aβ aggregate is indicative of Aβ-induced cytotoxicity.

As used herein, the phrase "determining the level of cytotoxicity" refers to quantitating the cytotoxic effect of the Aβ aggregates on a susceptible cell culture either in the presence or absence of a test agent or a control agent. The level of cytotoxicity can be measured using any method known in the art, and as described herein. For example, the level of cytotoxicity can be measured as the level of lactate dehydrogenase present in the culture medium or using other well known spectrophotometric assays, such as MTT. Alternatively, cytotoxicity can be measured as the number of apoptotic cells in the culture, or determined by measuring membrane integrity of the cells using various dyes such as trypan blue, acridine orange, or propidium iodide.

As used herein the term "inhibits" Aβ-induced cytotoxicity refers to the ability of an agent to partially or totally block, decrease, prevent, delay, inactivate, desensitize, or down regulate Aβ-induced cytotoxicity. An agent is deemed to be an inhibitor of Aβ-induced cytotoxicity if the level of Aβ-induced cytotoxicity in the presence of the agent is detectably less than the level of cytotoxicity in the absence of the agent. Means for detecting cytotoxicity are disclosed herein.

As used herein, the term "contacting" refers to the apparent touching or mutual tangency of Aβ or an Aβ aggregate with a cell, test agent, or control agent. The contacting can be done by any means known to persons skilled in the art. For example, contacting can be done mixing the components in a small volume of the same solution, such as in a cell culture plate. Furthermore, contacting does not require that all components to be contacted are present at the same time. Rather, it suffices that all components to be contacted are present together at some point during the assay or treatment. It is also to be recognized that the contacting can be accomplished in vitro or in vivo.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

As used herein the term "proteinaceous complex" as used herein refers to a composition comprising a protein component and a non-protein component. The protein component can include post-translational modifications such as glycosylation and glycation. The non-protein component can include a small organic molecule, a lipid, a nucleic acid, or a carbohydrate, etc.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 10 to 600, usually about 25 to about 250, more usually about 50 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). For the purposes of this invention, BLAST and BLAST 2.0 are used with default parameters to determine percent sequence identity for the nucleic acids and proteins of the invention. Software for performing BLAST analyses is publicly available through the National Center for Biotechnology Information (NCBI). The BLASTN program (for nucleotide sequences) uses as defaults a wordlength (W) of 11, an expectation (E) of 10, a cutoff of 100, M=5, N=−4, and a comparison of both strands. For amino acid (protein) sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915)). For the purposes of this invention, the BLAST2.0 algorithm is used with the default parameters, and with the filter off.

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, e.g., where the two peptides differ only by conservative substitutions.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, engineered antibody fragments and antibody based scaffolds such as mini-bodies, diabodies, triabodies, tetrabodies and nanobodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:* 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein the phrase "intravenous immunoglobulin" or "IVIG" refers to gamma globulin preparations suitable for intravenous use. Typically an IVIG product is prepared from crude plasma or from a crude plasma protein fraction obtained from human normal immunoglobulin (HNI), as described in U.S. Pat. No. 7,138,120.

As used herein, the phrase "therapeutically effective amount" refers to an amount of the agent that is sufficient to effectuate a desired therapeutic effect on a given condition or disease. Such amount can vary depending on the particular agent, the effect to be achieved, the mode of administration, etc.

General Methodology

Amyloid β Monomers

Aβ monomeric peptides suitable for producing aggregates for use in the invention can be synthetic, recombinant, or isolated from natural sources. In some embodiments the NH-terminal amino acid residue of the Aβ peptide corresponds to the aspartic acid residue at position 672 of the 770 amino acid residue form of the naturally occurring amyloid precursor protein (APP). Non-limiting exemplary Aβ peptides suitable for use with the invention include Aβ peptides having 39-43 amino acids (i.e. $A\beta_{1-39}$, $A\beta_{1-40}$, $A\beta_{1-41}$, $A\beta_{1-42}$, and $A\beta_{1-43}$). In some embodiments the 43 amino acid long form of the $A\beta_{1-43}$ protein has the amino acid sequence: DAEFRHDS-GYEVHHQKLVFFAEDVGSNKGAIIGLMVGGVVIAT.

In some embodiments shorter forms of the $A\beta_{1-43}$ protein are used. In some embodiments one or more (typically 1 to 4) amino acid residues are removed from the carboxy-terminal end of $A\beta_{1-43}$ (e.g., $A\beta_{1-39}$, $A\beta_{1-40}$, $A\beta_{1-41}$, or $A\beta_{1-42}$). In some embodiments, one or more amino acid residues are removed from the NH terminal end of the $A\beta_{1-43}$ protein. In some embodiments, one or more amino acid residues are removed from both the NH-terminal end and the carboxy terminal end of the $A\beta_{1-43}$ protein (e.g., $A\beta_{25-35}$). It is understood that variants of the $A\beta_{1-43}$ protein having deletions, additions, or conservative substitutions are also encompassed by the invention as long as the Aβ peptide is capable of forming aggregates that induce cytotoxicity in susceptible cell types using the methods disclosed herein. The Aβ peptides suitable for producing aggregates for use with the invention can be obtained from a variety of sources, including recombinantly produced, synthesized, isolated from natural sources, or purchased from commercial vendors (e.g., American Peptide Inc, Sunnyvale Calif., USA).

Production and Characterization of Aβ Aggregates

Methods for producing Aβ aggregates suitable for use with the invention are well known in the art, for example as described in Findeis, et al. (1999) *Biochemistry* 38:6791-6800. Typically, the aggregation is carried out by dissolving the Aβ peptide in a suitable buffer, and shaking the solution vigorously for a variable amount of time until the desired aggregation has been achieved. Suitable buffers may include any physiologically acceptable buffer, as known to a person of skill in the art. A non-limiting exemplary buffer suitable for use with the invention is described in Example 1. In some embodiments, the buffer may comprise the same tissue culture medium in which the cytotoxicity assay is conducted.

After dissolving the Aβ monomer in the buffer, the solution is shaken vigorously. This can be accomplished using any method known in the art. For example, the solution can be shaken at 700-800 rpm using a shaker platform, or alternatively, the solution can be vortexed and/or sonicated as described in Example 1. Additional methods of shaking the solution will be well known to persons of skill in the art. The amount of time that the solution is shaken can vary. In some embodiments, the solution can be shaken for as short a time as 1 minute, or as long as 1 hour or more. In some embodiments, the solution is shaken, monitored for aggregate formation, and the cycle repeated until the desired aggregate composition is obtained. In some embodiments, prior to the dissolution of the monomer in the appropriate buffer, the Aβ is treated to obtain a random coil monomer. This can be accomplished by treating the Aβ peptide with hexafluoroisopropyl alcohol (HFIPA) as described in U.S. Pat. App. No. 20020004194, or by treating with an acid as described in Findeis et al. (1999).

Once an Aβ aggregate is produced using any method known in the art, or as described herein, the aggregates are characterized prior to use in the screening assay. Characterization of the Aβ aggregates can be done using a variety of assays known in the art. Non-limiting exemplary methods of detecting and characterizing the aggregates suitable for use with the invention include fluorometric analysis using the thioflavin T or thioflavin S fluorescent dyes as disclosed in Du et al. (2003) *Brain* 126:1935-1939; M. Bourhima et al. (2007) *J. Neurosci. Meth.* 160(2): 264-268. A particular example detailing the characterization state of an Aβ aggregate preparation using a thioflavin T fluorometric assay is described in Example 1. Additional non-limiting assays suitable for use to detect and characterize Aβ aggregates that are known to persons of skill in the art include optical density assays, dye binding assays, static aggregation assays, gel electrophoresis assays and direct aggregate visualization using electron microscopy, as disclosed in U.S. Pat Pub. No. 2002/0098173 and in PCT Int'l Pat Pub. No. WO 2007/094668. Additional assays and methods for characterizing the Aβ aggregates suitable for use with the invention are known to persons of skill in the art.

Test Agents

Another component of the screening assay is a test agent that is to be screened for ability to inhibit the cytotoxic effect of the Aβ aggregates on a susceptible cell. A test agent suitable for screening with the assay can be any molecule, macromolecule, or complex mixture of molecules and macromolecules.

In some embodiments the test agent is an IVIG product. Numerous IVIG products are known in the art and described in for example, U.S. Pat. No. 7,138,120. Typically, an IVIG-preparation suitable for use with the invention are at least 95% IgG, with not more than 5% non-IgG-contaminating proteins.

In some embodiments, the test agent is an isolated protein or polypeptide. Non-limiting examples of proteins or polypeptides that can be used as test agents in the present invention include blocking peptides (for example fragments of the Aβ or APP that do not form aggregates with each other), an antibody, an Fab, or a ScFv that binds to Aβ, or binds to a cell and thereby blocks Aβ aggregate from interacting with the cell. The antibodies can be monoclonal or polyclonal, and can also be part of a complex mixture such as in IVIG. In some embodiments, the test agent is a non-protein molecule, such as a lipid, a steroid compound, or a carbohydrate. In some embodiments, the test agent is a protein or oligopeptides. In some embodiments, the protein test agent comprises protein molecules with and without post-translational modifications such as glycosylation and glycation. In some embodiments, the test agent is a macromolecule comprising a protein component and a non-protein component. Non-limiting exemplary macromolecular protein complexes can include protein-nucleic acid complexes (such as RNA and/or DNA), membrane-protein complexes, protein-lipid complexes, and protein-carbohydrate complexes. In some embodiments, the test agent is conjugated to a small molecule. In some embodiments, the test agent is a small molecule.

Control Agents

Another component of the screening assay is a control agent, against which the effect of the test agent can be normalized. The control agent can be any molecule or macromolecule that has been demonstrated to inhibit Aβ-induced cytotoxicity. A control agent is deemed to inhibit Aβ-induced cytotoxicity when the level of cytotoxicity in the presence of the control agent is statistically less than the level of cytotoxicity in the absence of the control agent. An exemplary control agent suitable for use with the present invention is an anti-amyloid β antibody.

Cell Culture and Growth Conditions

The screening assay of the invention is carried out in vitro using a susceptible cell type. Cells suitable for use with the screening assays of the invention include any cell that is susceptible to Aβ-induced cytotoxicity. Such cells are known to persons of skill in the art, and can be identified using the methods disclosed herein. For example, a cell culture that shows decreased viability (or increased cytotoxicity) when incubated in the presence of the Aβ aggregates as described herein, as compared to incubation in the absence of the Aβ aggregates is a cell type that is susceptible to Aβ-induced cytotoxicity that can be used with the screening assays of the invention. In some embodiments, the concentration of Aβ aggregates that is used to induce a cytotoxic response in a susceptible cell is in the range from about 2.5 μM to about 25 μM. Non-limiting exemplary cells suitable for use with the screening assays of the invention include the rat pheochromocytoma cell line PC-12 available from the American Type Culture Collection, Rockville Md. (ATCC CRL 1721). An additional cell line suitable for use with the present invention is the human neuronal derived cell line NT2 also available from the American Type Culture Collection (ATCC CRL 1973). The skilled artisan will know of additional cell types that can be used with the invention or can identify such cell types using the methods described herein, without undue experimentation.

The control and test cultures of the assay are grown using standard culture conditions and methods known to a person of skill in the art. See, e.g., R. Ian Freshney, *Culture of Animal cells: A manual of basic techniques*, Wiley-Liss, (1987). In some embodiments, the cells are grown in the presence of serum, and then switched to serum-free conditions prior to conducting the screening test. In some embodiments, the cells are grown and maintained in serum-free conditions. Suitable culture conditions for PC-12 cells are detailed in Example 2.

Screening Assay

The components of the screening assay have been described above. Suitable procedures for conducting the screening assay are described below. At a minimum, the assay requires a cell culture comprising a cell susceptible to Aβ induced cytotoxicity, a solution comprising Aβ aggregates in sufficient concentration to induce cytotoxicity in the susceptible cells, and a test agent. In some embodiments, additional steps or components may be added, while in other embodiments some optional components or embodiments may be omitted. For example, in some embodiments, the assay is conducted using a single culture, while in other embodiments, assay is conducted in a high-throughput format using multiple cultures such as in a 96 or 384 well plate. Examples 2 and 3 details variations of the screening assay that are suitable for use with the invention. Additional variations are described below and will be recognized by a person of skill in the art.

In some embodiments, the assay is conducted by mixing the test agent with a solution of Aβ aggregates, and then contacting the mixture to a cell in the test culture which is then incubated for a specified time period. Typically the incubation period ranges from 2 hours to 48 hours. In some embodiments, the cell culture is treated with a test (or a control) agent prior to addition of the Aβ aggregates. In some embodiments, the Aβ aggregates may be added to the cell culture before the addition of a test (or a control) agent. In some embodiments, the Aβ aggregates and a test (or a control) agent are added simultaneously to the cell culture without pre-mixing. In some embodiments, the concentration of the Aβ aggregate is in the range from about 2.5 μM to about 25 μM.

In some embodiments, a control culture is carried out in parallel with the test culture, with the only difference between the control and test culture being that the test agent is replaced with a control agent in the control culture. A control agent can be any compound, molecule, or macromolecular complex or mixture that has been shown to inhibit Aβ-induced cytotoxicity, as described herein. In some embodiments, the control agent is an anti-Aβ antibody. In some embodiments, a test agent that is shown to be effective for inhibiting Aβ-induced cytotoxicity can be used as a control agent in a subsequent assay. In some embodiments, the control culture is identical to the test culture, but without the test agent (i.e. a control culture can include the Aβ aggregates alone with the susceptible cells).

In some embodiments the assay is carried out using equal molar concentrations of the control agent and the test agent. In some embodiments, different concentrations of test agent are compared to a single concentration of control agent. In some embodiments the control agent and the test agent are added in a molar concentration ratio with the Aβ aggregates. In some embodiments, the molar concentration ratio of the agent:Aβ aggregate is in a range from about 1:30 to about 30:1. In some embodiments, the molar concentration ratio is 1:1.

At the end of the incubation period, the culture (test and/or control) is examined to determine the level of cytotoxicity. In some embodiments, a maximal level of cytotoxicity is determined by contacting a cell culture with the aggregated Aβ solution in the absence of a test or control agent. In some embodiments, the level of cytotoxicity in the test culture is expressed as a percentage of the level of cytotoxicity in the control culture. Additional methods for measuring and comparing the level of cytotoxicity in the cultures are described in examples 2 and 3.

Determining Aβ-Induced Cytotoxicity

Following incubation of the test and or control culture with the Aβ aggregates as described above, the level of Aβ-induced cytotoxicity in the culture is determined. A variety of assays for determining cell viability are commercially available and known in the art. Non-limiting exemplary viability assays suitable for use with the invention include spectrophotometric determination of the level of lactate dehydrogenase (LDH) from the culture medium using a "Cytotoxicity Detection Kit (LDH)" (Roche Diagnostics, Mannheim, Germany) as described in Examples 2 and 3. Alternatively, the cell viability can be determined by measuring mitochondrial dehydrogenase (MTT) using a commercially available detection kit (Sigma-Aldrich, St. Louis, Mo.) as described in U.S. Pat Pub. No. 20020004194. Additional assays for measuring cell viability are well known to persons of skill in the art as disclosed in Shearman, M. S. et al. (1994) *Proc. Natl. Acad. Sci. USA* 91:1470-1474; Hansen M. B. et al. (1989) *J. Immunol. Meth.* 1(19)203-210.

Recording the Results of Assays of the Invention

The methods of the invention may also involve recording the results of the screening assays of the invention. This information may be stored in a computer readable form. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system also be linked to a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of a cytotoxicity assay. In some embodiments, the computer system also comprises code for interpreting the results of the assay. Thus in an exemplary embodiment, the screening assay results are provided to a computer where a central processor is executes a computer program for determining the ability of a test agent to inhibit the cytotoxic effect of the Aβ aggregates on a susceptible cell, as compared to a control.

The invention also provides the use of a computer system, such as that described above, which comprises: (1) a computer; (2) a stored bit pattern encoding the genotyping results obtained by the methods of the invention, which may be stored in the computer; (3) and, optionally, (4) a program for determining the ability of a test agent to inhibit the cytotoxic effect of the Aβ aggregates.

Selecting an Agent that Inhibits Aβ-Induced Cytotoxicity.

After determining the level of cytotoxicity in the test and/or control cultures, suitable test agents can be selected which can then be further optimized, tested, or used to administer to a patient having AD. In some embodiments, the agent is identified by comparing the level of Aβ-induced cytotoxicity in the presence of the test agent with the level of Aβ-induced cytotoxicity in a control culture comprising a control agent or Aβ aggregates alone. In some embodiments, a test agent is deemed to inhibit Aβ-induced cytotoxicity when the level of cytotoxicity in the presence of the test agent is detectably less than the level of cytotoxicity in a control culture. In some embodiments, a test agent is deemed to inhibit Aβ-induced cytotoxicity when the level of cytotoxicity in the presence of the test agent is at least 5% less than the level of cytotoxicity in a control culture comprising a control agent or Aβ aggregates alone. In some embodiments a test agent is selected when the level of Aβ-induced cytotoxicity in the presence of the test agent is reduced at least 10%, 20%, 30%, 40%, 50%, 60%, 70%, 80%, 90%, or more compared to the level of cytotoxicity in a control culture comprising a control agent or the Aβ aggregates alone. Additional formulas and methods for comparing and selecting test agents that inhibit Aβ-induced cytotoxicity are detailed in Examples 2 and 3.

Therapeutic Methods and Pharmaceutical Compositions

Using the screening assays as described herein, various therapeutic test agents can be identified that inhibit Aβ-induced cytotoxicity in vitro. As described in more detail below, it is explicitly contemplated that the inhibitory agents selected using the assays described herein can be further optimized for administration, optionally with pharmaceutical carriers, in any suitable manner for the treatment of patients suffering from Alzheimer's disease (AD), or similar diseases involving Aβ-induced toxicity. In some embodiments, the screening methods are used to pre-select IVIG product lots for administering to patients with AD. Protocols for the administration of inhibitory agents are known, and can be further optimized for AD patients based on principles known in the pharmacological arts (see, *Remington's Pharmaceutical Sciences,* 18th ed., Mack Publishing Co., Easton, Pa., 1990).

The inhibitors identified using the screening assays of the invention can be administered to a patient at therapeutically effective doses to prevent, treat, or control Aβ-induced cytotoxicity. The compounds can be administered to a patient in an amount sufficient to elicit an effective protective or therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular inhibitor employed, condition of the subject, and route of administration. The size of the dose also will be determined by the existence, nature, and extent of any adverse effects that accompany the administration of a particular compound in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. In general, the dose equivalent of a modulator is from about 1 ng/kg to 100 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, that are well known to persons of ordinary skill in the art. Tablets can be coated by methods well known in the art. Liquid preparations for oral administration can take the form of, for example, solutions, syrups, or suspensions, or they can be presented as a dry product for constitution with water or other suitable vehicle before use and can include pharmaceutically acceptable additives as are well known to persons of ordinary skill in the art.

The compounds can be formulated for parenteral administration by injection, for example, by bolus injection or continuous infusion. Formulations for injection can be presented in unit dosage form, for example, in ampoules or in multidose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use. Additional modes of administration and formulations for pharmaceutical compositions suitable for use with agents identified using the screening assays of the invention are well known to persons of ordinary skill in the art.

Kits for Use in Diagnostic and/or Prognostic Applications

The invention also provides kits for diagnostic or therapeutic applications. For diagnostic/prognostic applications, such kits may include any or all of the following: assay reagents, buffers, Aβ peptides or aggregate solutions, susceptible cell types, control agents, or the like.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are provided by way of illustration and not by way of limitation. Those of skill in the art will readily recognize a variety of non-critical parameters that could be changed or modified to yield essentially the same or similar results.

Example 1

Fluorometric Analysis of $A\beta_{1-42}$ Peptide

To confirm that $A\beta_{1-42}$ aggregates in vitro, we used a thioflavin T binding assay as described below. Lyophilized synthetic $A\beta_{1-42}$ peptide was obtained from American Peptide Inc. (Sunnyvale, Calif., USA). The $A\beta_{1-42}$ peptide was dissolved in 10 mM Tris/HCl buffer pH 8.6 to a final $A\beta_{1-42}$ concentration of 1 mg/ml. The $A\beta_{1-42}$ solution was vortexed violently for 1 minute, sonicated for 5 minutes, after which the pH was adjusted to neutral (6.8-7.4) using 0.1% HCl buffer.

The fluorometric analysis to assess the fibrillization state of the $A\beta_{1-42}$ preparation was done with a thioflavin T binding assay. See, Du et al. (2003) *Brain* 126:1935-1939. Briefly, thioflavin T binds β-sheet structures in proteins (e.g. in $A\beta_{1-42}$ aggregates) and thus an increase in thioflavin T fluorescence indicates an increased level of $A\beta_{1-42}$ aggregates in the solution. Thioflavin T (Sigma-Aldrich Chemical Co., St. Louis, Mo., USA) was used at a concentration of 2 μM in 50 mM glycine HCl buffer, pH 9.2. Aggregation measurements were carried out in 96 well microplates in triplicate using a Synergy 2 (BioTek, Winooski, Vt., USA) fluorimeter at excitation and emission wavelengths of 435 and 485 nm, respectively.

Example 2

Cytotoxicity Assay

To evaluate the cytotoxic effects of $A\beta_{42}$ on cells in vitro, we used the following assay. Rat pheochromocytoma PC-12 cells (ATCC Manassas, Va., USA) are known to be susceptible to Aβ-induced cytotoxicity. See, Solomon, B., et al. (1997) *Proc. Natl. Acad. Sci. USA* 94:4109-4112. The cells were adapted to serum-free conditions in Neurobasal culture medium with B27 serum substitute (Invitrogen, Carlsbad, Calif., USA) and 2 mM L-glutamine (Gibco-Invitrogen, UK). PC12 cells were collected from growth flasks, washed, and pelleted via centrifugation at 244×g. Cells were then resuspended and filtered through Cell Trics (20 μm) to remove cell aggregates. Filtered cells were seeded into microplates (100 μl/well) at a density of $1-1.5\times10^5$ cells/ml in medium supplemented with 1% human serum albumin (Baxter). Total volume per well for all experiments was 200 μl.

$A\beta_{42}$ peptide prepared as described in Example 1 above, was added to the wells containing cells at a concentration from about 2.5 μM to about 25 μM. Each assay was performed in quadruplicate.

Plates were incubated for 24 hours at 37° C. and 5% $CO_2$. After the 24 hour incubation period the plates were centrifuged at 300×g for 20 minutes and cell supernatants (100 μl/well) were aspirated for photometrical determination of Lactate Dehydrogenase (LDH).

Analysis of cytotoxicity was carried out using photometrical measurement of LDH released from the cells into the cell culture supernatant using a "Cytotoxicity Detection Kit (LDH)" (Roche Diagnostics, Mannheim, Germany) according to the manufactures instructions. LDH is a stable cytoplasmic enzyme present in all cells that is rapidly released into the cell culture supernatant upon damage of the plasma membrane. The kit consists of two components a catalyst (lyophilizate Diaphorase/NAD+ mixture) and a Dye solution (Iodotetrazolium chloride/sodium lactate). The LDH activity is determined in an enzymatic test. In the first step of the reaction NAD+ is reduced to NADH/H+ by the LDH-catalyzed conversion of lactate to pyruvate. In the second step, the catalyst (diaphorase) transfers H/H+ from NADH/H+ to the tetrazolium salt which is then reduced to formazan that is then measured at 492 nm (references is 620 nm). An increase in the amount of damaged cells results in an increased amount of LDH in the culture supernatant, which correlates to the amount of formazan formed during a limited time period. In the present example, the measurement was performed after 15 and 30 minutes of light protected incubation with the kit reagents.

To determine the percentage of cytotoxicity, the average absorbance values measured in triplicate were calculated. The background values from control culture media were subtracted from each average and the percentage cytotoxicity was determined using the following formula:

$$\frac{(\text{Experimental value} - \text{Spontaneous } LDH \text{ release})}{(\text{Maximum } LDH \text{ Release} - \text{Spontaneous } LDH \text{ Release})} \times 100\%$$

Maximum LDH release was achieved by the addition of 1% Triton X-100 solution to the cell culture for 2 hours. As shown in FIG. 1, the Aβ$_{42}$ synthetic peptide was cytotoxic at concentrations ranging from 5 μM to 25 μM, with maximum at about 20 μM Example 3

Figure 2:
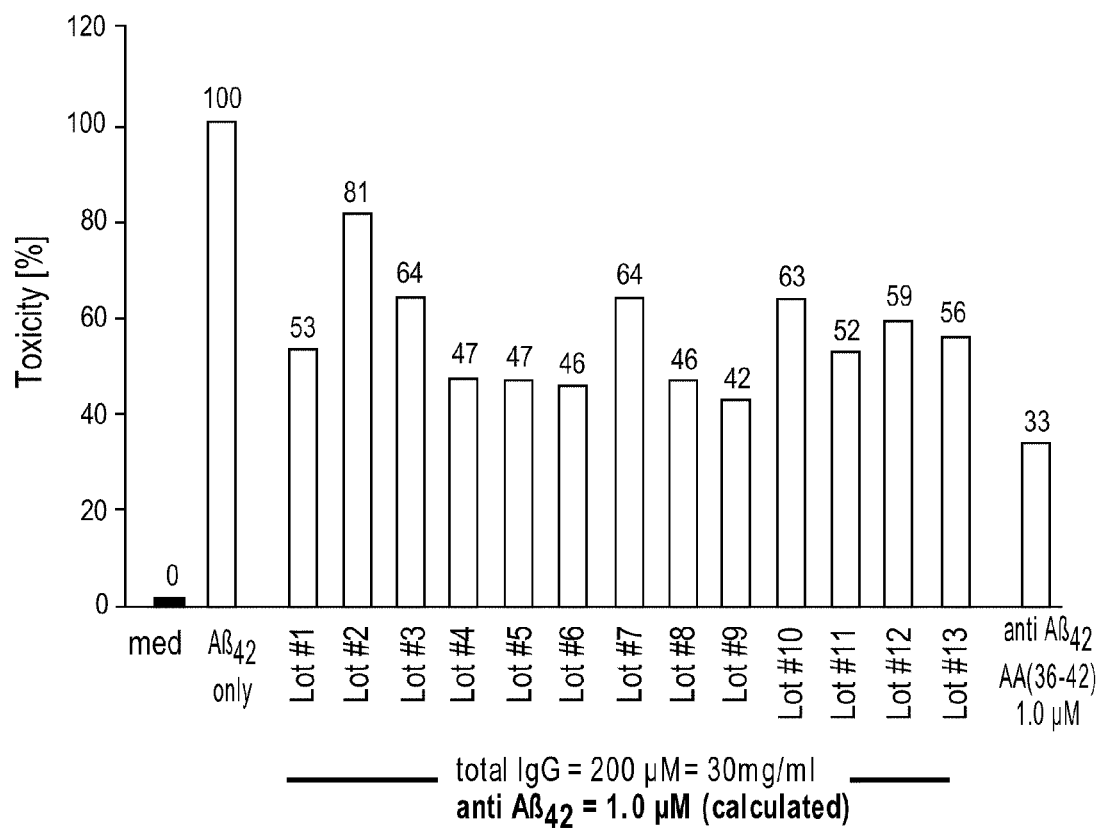
FIG. 2 shows the modulation of $A\beta_{42}$-induced cytotoxicity in vitro by 13 different lots of GAMMAGARD®, IVIG (lot#1-13). $A\beta_{42}$ peptide was pre-incubated with the 13 IVIG lots, the rabbit anti-$A\beta_{42}$ (AA36-42) polyclonal antibody, or medium, and then added to PC-12 cells (n=3). LDH release was measured after 24 hours of incubation. The spontaneous LDH release from PC-12 cells cultured in medium only (med) was calculated as 0% toxicity, the cytotoxicity induced by 10 μM $A\beta_{42}$ ($A\beta_{42}$ only) as 100% cytotoxicity. GAMMAGARD® was used in concentration 200 μM

Human Plasmatic IgG (IVIG) Reduces Aβ$_{42}$ Peptide Induced Cytotoxicity in Vitro This example demonstrates that the in vitro assay can be used to rapidly screen different lots of IVIG to identify those lots with the greatest neuroprotective effect against Aβ$_{1-42}$ induced cytotoxicity. GAMMAGARD®, IVIG (Baxter AG) was dialyzed against phosphate buffered saline (Gibco Invitrogen, Scotland, UK) at 4° C. overnight and subsequently diluted to obtain a final concentration of 200 μM, 133 μM and 67 μM. The Aβ$_{1-42}$ peptide as described above in Example 1 was incubated with GAMMAGARD®, IVIG for different time periods at 37° C. and 5% CO$_2$ before being added to the PC-12 cells cultured above as described in Example 2. The cells were incubated with Aβ$_{1-42}$ peptide (with or without GAMMAGARD®, IVIG) for 24 hours at 37° C. and 5% CO$_2$. Cytotoxicity was determined by measuring LDH release as described above in Example 2, with one modification. The LDH released by Ab42 in the absence of GAMMAGARD®, IVIG was considered as maximum LDH release (100%). The results are shown in FIG. 2.

These results suggest that different lots of GAMMAGARD®, IVIG might have different capacities to prevent Aβ-induced cytotoxicity in patients with AD. Therefore, preselection of suitable IVIG lots and products can improve the treatment of AD patients.

Example 4

Validation of the In Vitro Cytotoxicity Assay

The cytotoxicity assay was done as described in Example 2. The plates were incubated for 24 hours, and the cell supernatants were analyzed for LDH release.
Assessment of Intra-Assay Variation
The assay was done with six different lots of Gammagard Liquid and 14 replicates for each lot at a concentration of 200 μM. The intra-assay variation for each lot was calculated using the following equation:

$$CV_{intra-assay}(\%) = 100 \times \frac{SD \text{ of arithmetic mean}}{\text{arithmetic mean of the } OD}$$
obtained for 14 different samples The mean $CV_{intra-assay}$ for the six different lots was 2.9±1.4% (mean±SD)
Assessment of Inter-Assay Variation
The assay was done with five different lots of Gammagard Liquid on 8 different days (in quadruplicates) at a concentration of 200 μM. Inter-assay variation for each lot was calculated using the following equation:

$$CV_{inter-assay}(\%) = 100 \times \frac{SD \text{ of arithmetic mean in 8 experiments}}{\text{arithmetic mean of the } OD \text{ of samples in 8 experiments}}$$

The mean $CV_{inter-assay}$ for the five different Gammagard Liquid lots tested was 9.2±2.3% (mean±SD)

Example 5

Characterization of Synthetic Aβ$_{42}$ Peptide by Western Blot Analysis

Western blot analysis was done to investigate the aggregation status of the synthetic Aβ$_{42}$ peptide preparation. Aβ$_{42}$ peptide was analyzed by SDS-PAGE using NuPAGE Novex 4%-12% Bis-Tris gradient gels (Invitrogen, Carlsbad, Calif., USA). The subsequent Western blot analysis was done on nitrocellulose blotting membranes (Invitrogen, Carlsbad, Calif., USA), using the murine monoclonal IgG1 antibody 6E10 (Covance, Emeryville, Calif., USA) that recognizes all Aβ$_{42}$-conformers. Binding of the antibody was visualized using a goat anti-mouse IgG antibody that was conjugated to horseradish peroxidase (HRP, Sigma, St. Louis, Mo., USA) and a HRP-conjugate substrate kit (Bio-Rad, Hercules, Calif., USA).

Figure 3:
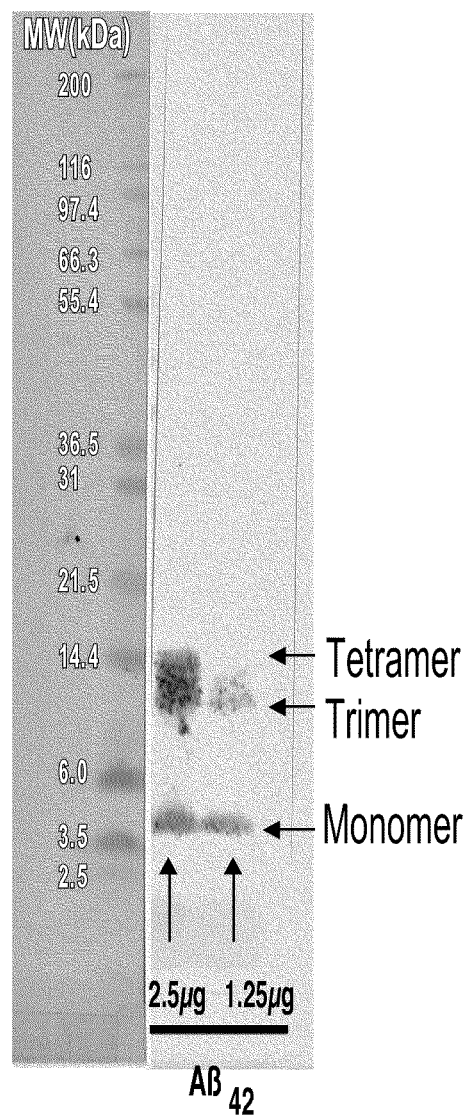
FIG. 3 shows characterization of synthetic $A\beta_{42}$ peptide by Western blot analysis. Synthetic $A\beta_{42}$ peptide was freshly dissolved, separated by SDS-PAGE and analyzed by Western blotting using the murine monoclonal anti-$A\beta_{42}$ antibody 6E10. 1.25 μg or 2.5 μg of $A\beta_{42}$ were used as starting material. The Western blot analysis shows that the synthetic $A\beta_{42}$ peptide consisted predominantly of small oligomers, trimers, and tetramers.

As shown in FIG. 3, the synthetic Aβ$_{42}$ peptide consisted predominantly of small oligomers, trimers, and tetramers. These forms represent the Aβ$_{42}$ species considered to be most relevant for neurotoxicity (see, Klein et al., (2001) Trends Neurosci 24:219-24).

Example 6

Concentration-Dependent Modulation of Aβ$_{42}$-Induced Neurotoxicity by IVIG

Figure 4:
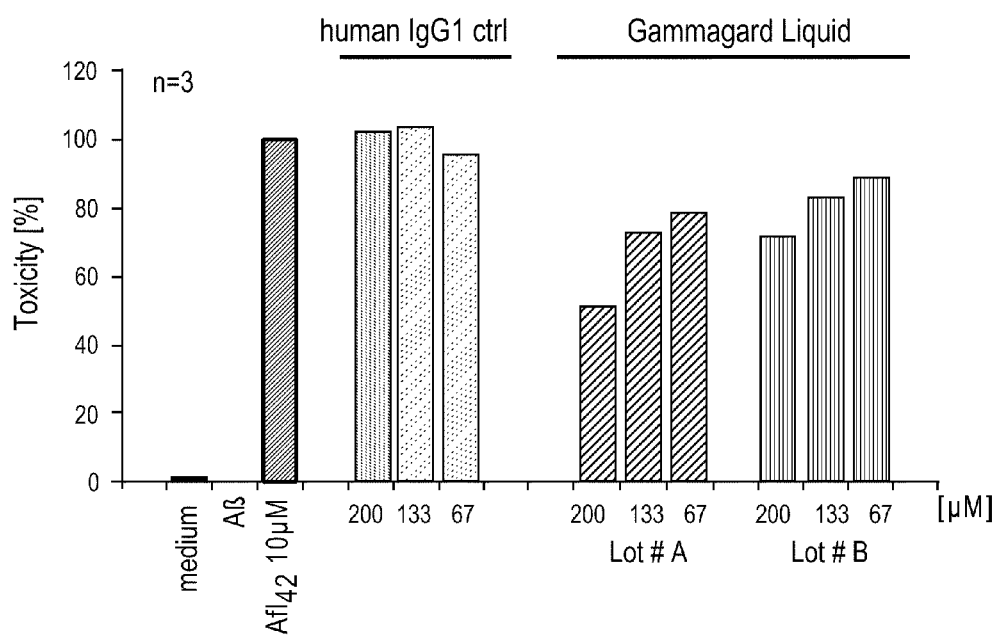
FIG. 4 shows concentration-dependent modulation of $A\beta_{42}$—induced cytotoxicity by GAMMAGARD® Liquid. $A\beta_{42}$ peptide was pre-incubated with two IVIG lots, the IgG1 control antibody, or medium for 40 min, and then added to PC-12 cells (n=3). LDH release was measured after 24 hours of incubation. $A\beta_{42}$-induced neurotoxicity was set at 100% for data analysis. GAMMAGARD® Liquid resulted in a concentration-dependent reduction of $A\beta_{42}$-induced neurotoxicity in vitro, while the human IgG1 control antibody was not effective at any concentration tested.

The cytotoxicity assay was done as described in Example 3. Before being added to the PC-12 cells the Aβ$_{42}$ peptide (10 μM) was pre-incubated with two different lots of Gammagard Liquid and a human IgG1 antibody, directed against a non-Aβ-related protein, served as a negative control. The final concentrations of the IVIG and of the IgG1 antibody were 200 μM (corresponding to 30 mg/ml), 133 μM (20 mg/ml) and 67 μM (10 mg/ml). The cell culture plates were incubated with Aβ$_{42}$ peptide (with or without Gammagard) for 24 hours. To determine the percentage of cytotoxicity, the calculations were done as in Example -3. As shown in FIG. 4, Gammagard Liquid resulted in a concentration-dependent reduction of Aβ$_{42}$-induced neurotoxicity in vitro, while the human IgG1 control antibody was not effective at any concentration tested.

Example 7

Figure 5:
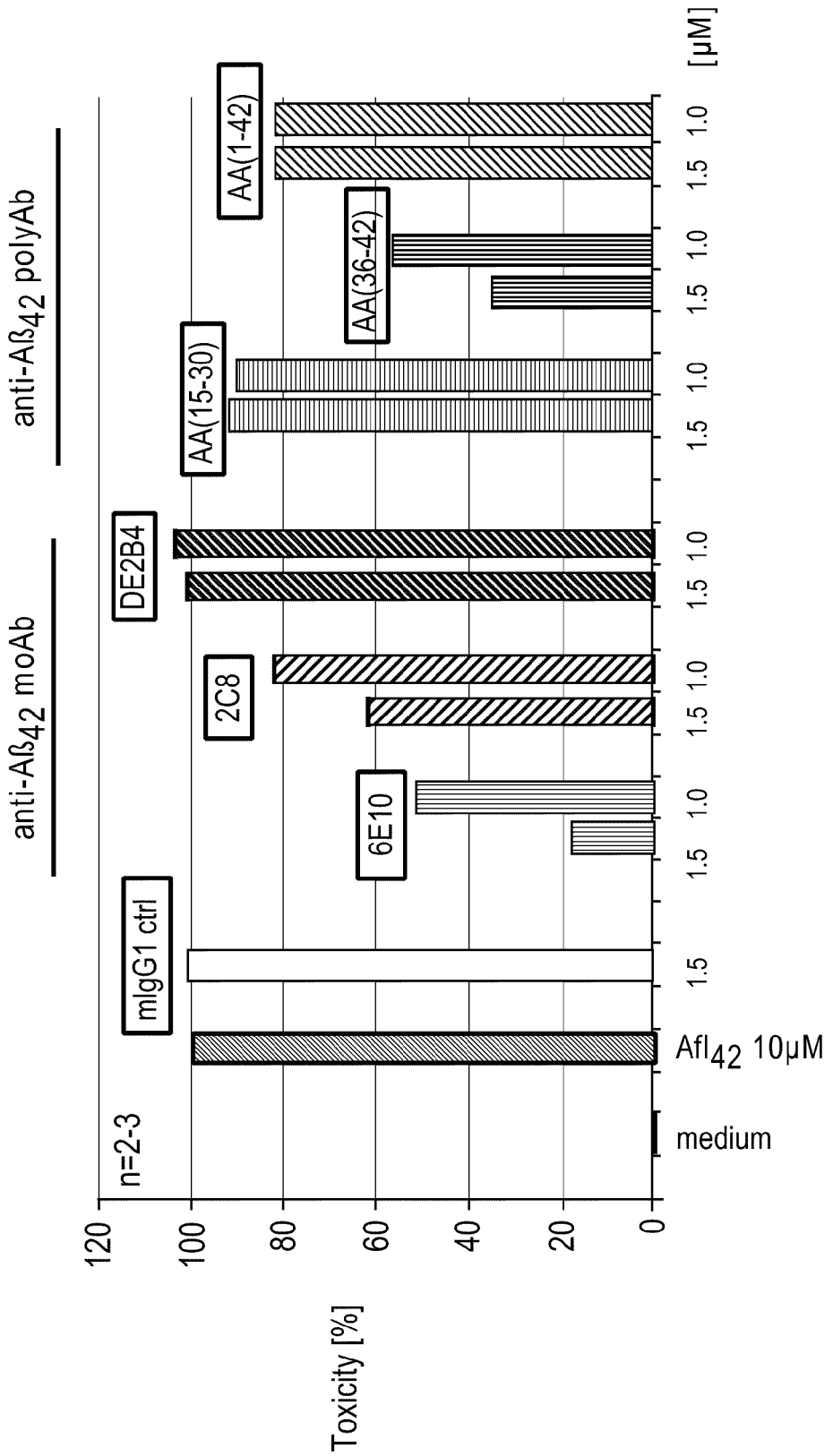
FIG. 5 shows modulation of $A\beta_{42}$-induced neurotoxicity by commercially available anti-$A\beta_{42}$ antibodies. Freshly dissolved synthetic $A\beta_{42}$ peptide was preincubated with monoclonal (moAb) anti-Aβ42 antibodies, a murine IgG1 control antibody (mIgG1ctrl) or medium for 40 min and subsequently added to PC-12 cells. LDH release was measured after 24 hours. The spontaneous LDH release from PC-12 cells cultured in medium only was calculated as 0% toxicity, the cytotoxicity induced by 10 μM $A\beta_{42}$ as 100% cytotoxicity. The monoclonal antibody 6E10, that recognizes the N-terminal epitope AA 3-8 from $A\beta_{42}$, showed the best protection. The negative control antibody had no effect.

Modulation of Aβ42-Induced Neurotoxicity by Commercially Available Anti-Aβ42 Antibodies The following commercially available anti-Aβ42 antibodies were tested for their ability to interfere with Aβ42-induced neurotoxicity:
Monoclonal antibodies: 6E10 (murine IgG1), directed against the N-terminal peptide AA 1-16 (Covance, Emeryville, Calif., USA); DE2B4 (murine IgG1), directed against the N-terminal peptide AA 1-17 (Serotec, MorphoSys, UK); 2C8 (murine IgG2b), directed against the N-terminal peptide AA 1-16 (MBL, Naka-ku Nagoya, Japan). A murine IgG1 antibody, directed against KLH (R&D Systems, Minneapolis, Minn., USA) was used as negative control.
Polyclonal antibodies: rabbit IgG, directed against full length peptide AA 1-43 (Santa Cruz Biotechnology, Santa Cruz, Calif., USA); rabbit Ig, directed against peptide AA 15-30 (Biosource, Camarillo, Calif., USA); rabbit Ig, directed against peptide AA 36-42 (Biosource, Camarillo, Calif., USA).
The fibrillization status of freshly dissolved Aβ$_{42}$ peptide was analyzed by fluorimetric measurement. Aβ$_{42}$ peptide was added to the cells with or without preincubation with the monoclonal antibodies. The plates were incubated for 24 hours, and the cell supernatants were analyzed for LDH release.
To determine the percentage of cytotoxicity, the calculations were done as in Example-3. FIG. 5 shows that commercially available monoclonal and polyclonal antibodies differ in their ability to prevent $A\beta_{42}$-induced neurotoxicity in vitro, while the control IgG1 antibody had no effect.

All patents, patent applications, and other publications, including published amino acid or polynucleotide sequences are hereby incorporated by reference in their entirety for all purposes not inconsistent with the teachings as disclosed herein.

What is claimed is:

1. A method of preparing a pharmaceutical composition comprising IVIG in a therapeutically effective dose for treatment of Alzheimer's Disease, the method comprising:
   a) contacting a first test cell culture with a cytotoxic Aβ aggregate and a first sample from a first IVIG lot,
   b) contacting a second test cell culture with a cytotoxic Aβ aggregate and a second sample from a second IVIG lot,
   c) detecting the level of cytotoxicity in the first and second test cell cultures, and
   d) comparing the level of cytotoxicity in the first test culture with the level of cytotoxicity in the second test cell culture,
   e) preparing a pharmaceutical composition comprising IVIG in a therapeutically effective dose for treatment of Alzheimer's Disease only from the IVIG lot having a higher level of inhibition of cytotoxicity.

2. The method of claim 1, further comprising the step of determining the level of cytotoxicity in a control cell culture.

3. The method of claim 2, wherein the control cell culture further comprises a cytotoxic Aβ aggregate.

4. The method of claim 3, wherein the control cell culture further comprises a control agent known to inhibit Aβ-induced cytotoxicity.

5. The method of claim 1, wherein the first and second samples are contacted with the first and second test cell cultures before the cytotoxic Aβ aggregates.

6. The method of claim 1, wherein the cytotoxic Aβ aggregates are contacted with the first and second test cell cultures before the first and second samples.

7. The method of claim 1, wherein the first and second samples and the cytotoxic Aβ aggregates are pre-mixed before contacting the first and second test cell cultures.

8. The method of claim 2, wherein the first and second test cell cultures and the control cell culture are grown under serum-free conditions.

9. The method of claim 3, wherein the first and second test cell cultures and the control cell culture comprise PC-12 cells.

10. The method of claim 4, wherein the control agent is an anti-Aβ antibody.

11. The method of claim 1, wherein the Aβ aggregates are comprised of Aβ-40 or Aβ1-42.

12. The method of claim 1, wherein the cytotoxic aggregates are comprised of at least an Aβ dimer.

13. The method of claim 12, wherein a fibril content of the cytotoxic Aβ aggregate is quantitated using a thioflavin T fluorescence assay.

14. The method of claim 1, wherein the cytotoxic Aβ aggregates are present in a concentration range from about 2.5 μM to about 25 μM.

15. The method of claim 1, wherein the cytotoxic Aβ aggregates are present in a concentration range from about 5 μM to about 30 μM.

16. The method of claim 1, wherein the cytotoxic Aβ aggregates are present in a concentration range from about 10 μM to about 15 μM.

17. The method of claim 4, wherein the first sample in the first test cell culture, the second sample in the second test cell culture, and the control agent in the control cell culture are all present in equal molar concentrations.

18. The method of claim 17, wherein the first sample in the first test cell culture, the second sample in the second test cell culture, and the control agent in the control cell culture are all present in a range of molar concentration ratios with the cytotoxic AP aggregate from about 30:1 to about 1:30.

19. The method of claim 1, wherein the level of cytotoxicity is determined by measuring the concentration of lactate dehydrogenase in the culture media.

20. The method of claim 1, wherein the level of cytotoxicity is determined by measuring the level of apoptosis in the cell culture.

* * * * *